United States Patent [19]
Lakatos et al.

[11] Patent Number: 5,792,164
[45] Date of Patent: Aug. 11, 1998

[54] SURGICAL INSTRUMENT

[76] Inventors: Nick Lakatos, 1625 Elm St., Des Plaines, Ill. 60018; Harrith M. Hasson, 2043 N. Sedgwick, Chicago, Ill. 60614

[21] Appl. No.: 359,021

[22] Filed: Dec. 19, 1994

[51] Int. Cl.⁶ .................................................. A61B 17/00
[52] U.S. Cl. ................................................. 606/170; 606/206
[58] Field of Search .......................... 606/51, 52, 108, 606/170, 174, 205–211, 198; 128/3, 4, 6, 751–755

[56] References Cited

U.S. PATENT DOCUMENTS

| | | | |
|---|---|---|---|
| 4,872,456 | 10/1989 | Hasson . | |
| 4,880,015 | 11/1989 | Nierman | 128/751 |
| 5,282,826 | 2/1994 | Quadri | 606/207 |
| 5,330,502 | 7/1994 | Hassler et al. | 128/751 |
| 5,350,391 | 9/1994 | Iacovelli | 606/207 |
| 5,383,888 | 1/1995 | Zvenyatsky et al. | 128/751 |
| 5,454,827 | 10/1995 | Aust et al. | 128/751 |
| 5,468,250 | 11/1995 | Paraschac et al. | 128/751 |
| 5,490,819 | 2/1996 | Nicholas et al. . | |

*Primary Examiner*—Michael Buiz
*Assistant Examiner*—William Lewis
*Attorney, Agent, or Firm*—Wood, Phillips, VanSanten, Clark & Mortimer

[57] ABSTRACT

A surgical instrument having a body with a proximal end and a distal end, a working element, first structure for mounting the working element on the body for movement relative to the body between first and second positions, and second structure on the body for a) moving the working element selectively between the first and second position from a location remote from the working element and b) maintaining the working element in each of the first and second positions. The second structure includes an actuating element and third structure for mounting the actuating element on the body for movement relative to the body.

16 Claims, 2 Drawing Sheets

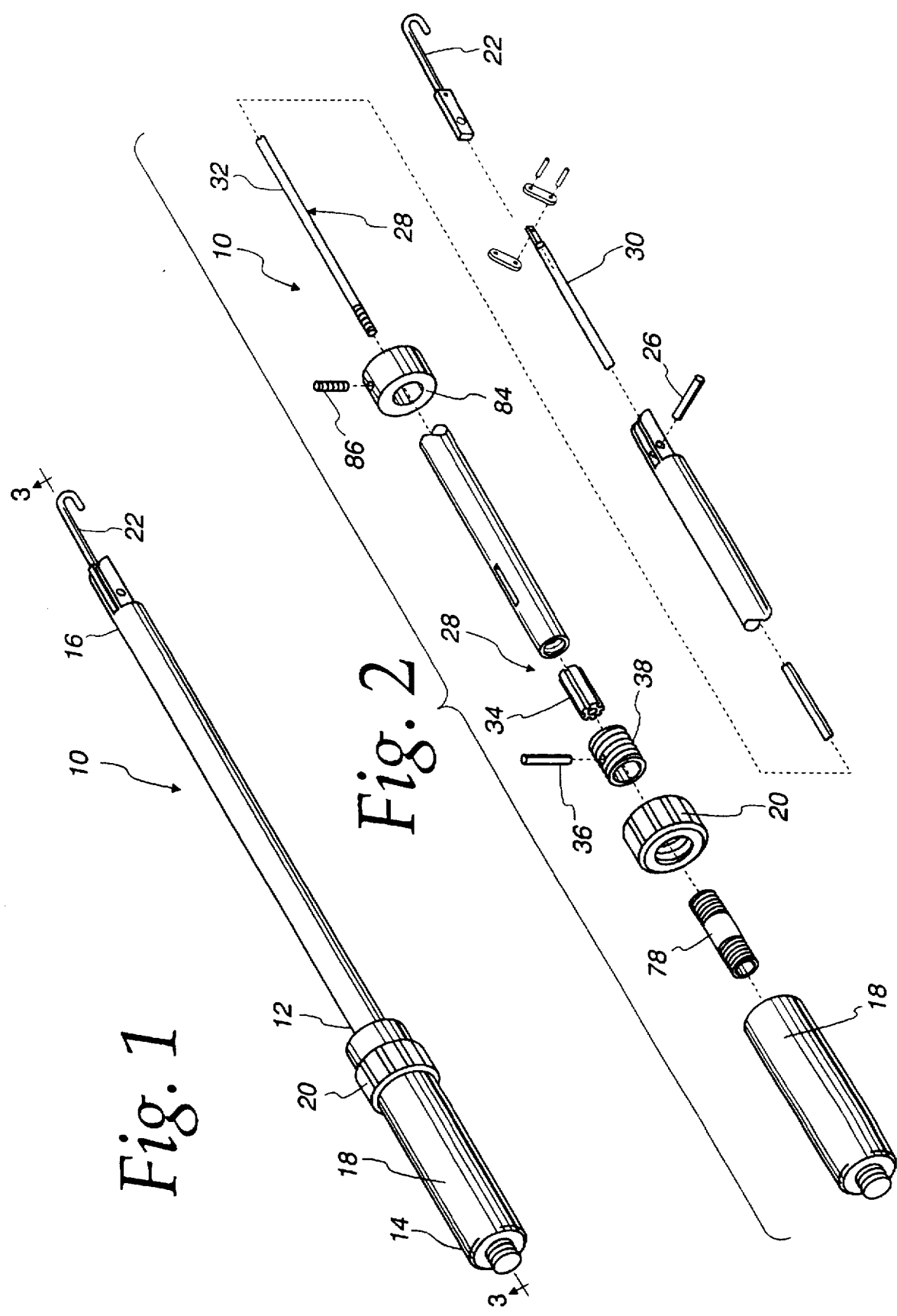

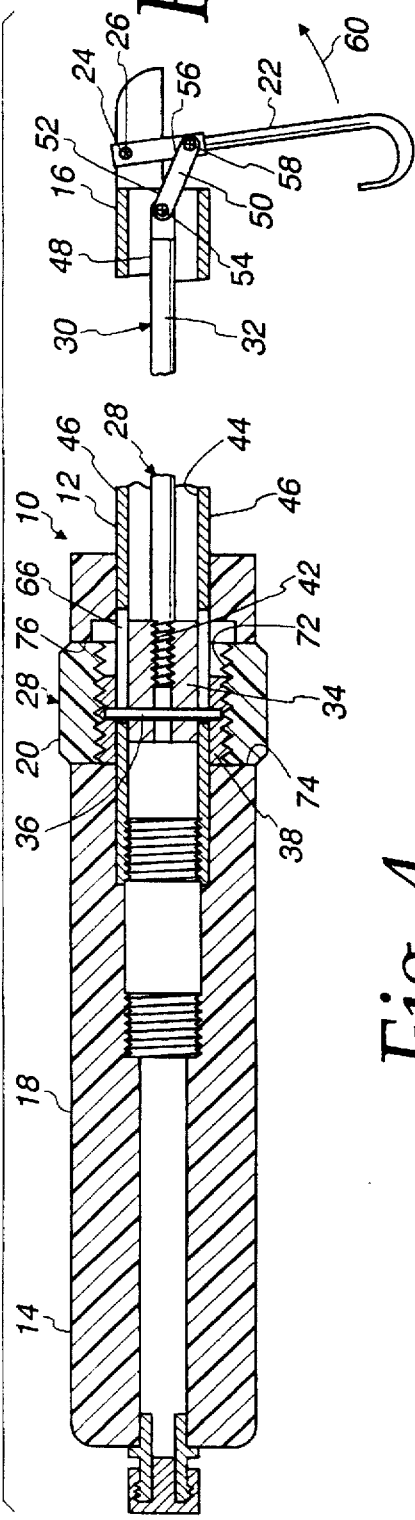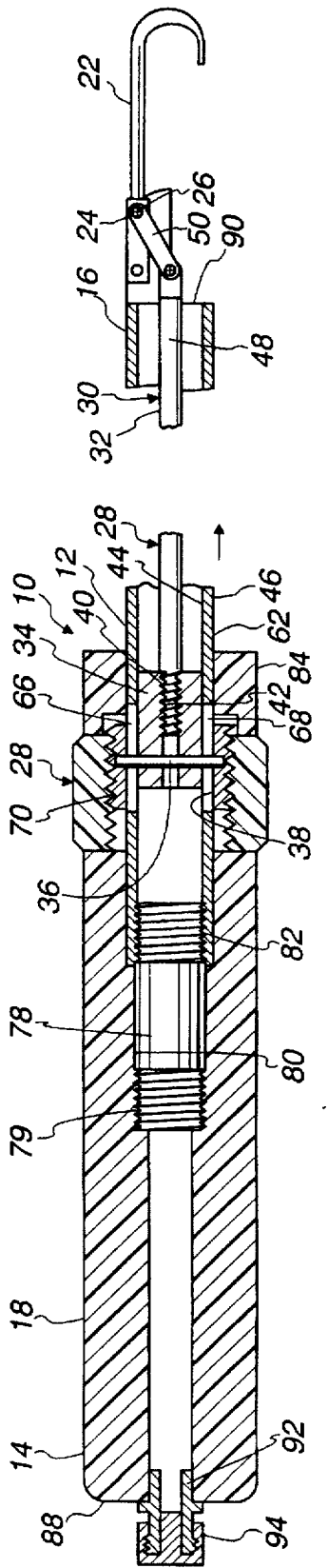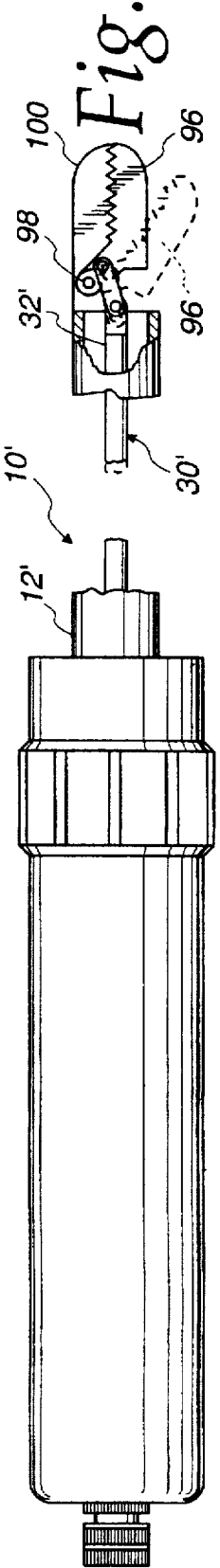

SURGICAL INSTRUMENT

BACKGROUND OF THE INVENTION

1. Field of the Invention

This invention relates to surgical instruments, such as those used during laparoscopy, and, more particularly, to a surgical instrument having a repositionable working element that can be selectively maintained in a plurality of different positions.

2. Background Art

There are a multitude of surgical instruments having a movable working element that is repositionable from a location remote therefrom. These instruments range in type from simple forceps to more complex manipulators, such as shown in my U.S. Pat. No. 4,944,741. While this type of instrument is commonly used during the performance of conventional procedures, it is highly useful in laparoscopy.

It is common to construct laparoscopic instruments with a sleeve that can be directed guidingly through a cannula and a mechanism, contained within the sleeve, for repositioning the working element. Commonly, this mechanism includes a rod that is slidable lengthwise within the sleeve to effect the requisite movement of the working element. Many of these instruments utilize a pair of pivotably joined grips, at the sleeve end opposite to which the working element is mounted, which grips are operated like the grips on a scissors to slide the rod within the confining sleeve.

Another feature common to this type of instrument is the ability to lock the working element in a desired position. This locking feature is important in that it may allow the surgeon to free his/her hand holding that instrument to engage another instrument or perform another task. This becomes very important in certain laparoscopic procedures in which several instruments are simultaneously directed into a working cavity and used in a coordinated fashion in carrying out a procedure.

It is known to provide an instrument with a pair of clamping jaws which can be used to grip a tissue, close a vessel, etc. In the absence of this locking mechanism, the surgeon is required to maintain a constant pressure on the operating grips or engage the services of another party to do this.

One known type of locking mechanism has cooperating teeth on the grips which define a ratchet-type mechanism. The locking teeth engage with the working element in a closed state. Continuing force application enhances the gripping force produced by the working element.

While this type of mechanism has proven effective in performing its intended function, it has a number of drawbacks. First of all, the ratchet engages only with the working element in a single, closed position.

Further, release of the locking mechanism requires that the grips initially be squeezed so that the gripping force is enhanced and thereafter relatively shifted in the line of the pivot axis for the grips to free the teeth and allow the working element to be opened. This requires that the surgeon's hand be contorted to an uncomfortable position. Aside from the discomfort associated with this movement, repetitions thereof tend to cause muscular fatigue which make it more difficult to perform subsequent procedures. The application of the squeezing force on the grips may be, itself, somewhat fatiguing.

A further problem with this type of mechanism is that damage may be inflicted to a vessel or organ in releasing the working element. For example, the locking element might be inadvertently engaged at a point in the procedure when only a light gripping force is in order. The surgeon is then required to enhance that gripping force to effect release. This increased force may be such as to sever the gripped organ or vessel.

In my U.S. Pat. No. 4,944,741, an instrument is shown wherein a set screw is used to fix the position of two relatively movable elements. The set screws tighten with the working element in its operating state.

While the set screw is a viable alternative to the above ratchet mechanism, it too has drawbacks. Most significantly, two hands are required to set and lock the instrument in its desired state. It is obviously inconvenient for the surgeon to have to dedicate his/her attention, and use both hands, to lock and release the working element.

It is also known to use springs to maintain a closing force on relatively movable jaws, or the like. Several different spring closing mechanisms are shown in my U.S. Pat. No. 5,250,056. While these mechanisms perform effectively, springs inherently are prone to weakening over time and after repeated usage.

A further problem with instruments having a working element that is operated using relatively movable grips is that the grips can only be comfortably operated with the instrument in a certain range of positions, i.e. through less than a 360° rotational range around the lengthwise axis of the instrument. This makes operation of the working element in certain positions, uncomfortable, and in certain other positions, impossible.

SUMMARY OF THE INVENTION

In one form of the invention, a surgical instrument is provided having a body with a proximal end and a distal end, a working element, first structure for mounting the working element on the body for movement relative to the body between first and second positions, and second structure on the body for a) moving the working element selectively between the first and second position from a location remote from the working element and b) maintaining the working element in each of the first and second positions. The second structure includes an actuating element and third structure for mounting the actuating element on the body for movement relative to the body.

The second structure may maintain the working element in a third position.

In one form, the second structure prevents the working element from moving from its second position towards its first position by manipulation of the working element.

The working element is movable from its first position towards its second position as an incident of the actuating element moving relative to the body in a first direction. In one form, the second structure allows the working element to move from its second position towards its first position only by moving the actuating element relative to the body oppositely to the first direction.

In one form, the third structure mounts the actuating element on the body for rotational movement relative to the body about a first axis.

The body may be elongate with a length that is substantially parallel to the first axis.

In one form, the first structure mounts the working element on the body for pivoting movement of the working element relative to the body about a second axis, which is transverse to the first axis.

In one form, the second structure includes a slide element and structure cooperating between the slide element and body for guiding translatory movement of the slide element relative to the body between first and second positions, with there being structure cooperating between the slide element and working element for moving the working element from the first position into its second position as an incident of the slide element moving from its first position into its second position.

With a rotatable actuating element, the slide element is movable from its first position into its second position as an incident of the actuating element rotating in one of first and second opposite directions. The slide element can be moved from its second position into its first position as an incident of the actuating element rotating in the other of the first and second opposite directions.

The structure cooperating between the actuating element and slide element may include cooperating threads on the actuating element and slide element.

The working element may take a variety of different forms. For example, it may include a first jaw which cooperates with a second jaw on the body. With the first jaw in the first position, the first and second jaws are closed against each other. With the first jaw in the second position, the first and second jaws are in an open state.

The body may have a cylindrical configuration, with the actuating element being in the form of an annular ring having an axis aligned substantially with the lengthwise axis of the body.

The body may have a passage therethrough to facilitate flushing of the surgical instrument. A removable cap can be used to block the body passage.

In another form of the invention, a surgical instrument is provided having a body, a working element, first structure for mounting the working element on the body for movement relative to the body between first and second positions, and second structure on the body for a) moving the working element selectively between the first and second positions from a location remote from the working element and b) preventing the working element from being moved relative to the body by manipulation of the working element.

The body may have a cylindrical shape that can be grasped by the hand of a user such that with the body grasped in one hand, a finger on the one hand can be used to operate the actuating element.

BRIEF DESCRIPTION OF THE DRAWINGS

FIG. 1 is a perspective view of a surgical instrument, according to the present invention;

FIG. 2 is an exploded perspective view of the inventive instrument;

FIG. 3 is an enlarged, cross-sectional view of the instrument taken along line 3—3 of FIG. 1 and showing the working element thereon in a first position;

FIG. 4 is a view as in FIG. 3 with the working element in a second position; and FIG. 5 is an enlarged, side elevation view of the inventive instrument with a modified form of working element.

DETAILED DESCRIPTION OF THE DRAWINGS

A surgical instrument, according to the present invention, is shown at 10 in FIGS. 1-4. The instrument 10 has an elongate, cylindrical body 12 with a proximal end 14 and a distal end 16.

At the proximal body end 14, a cylindrical grip 18 is defined. The grip 18 can be comfortably grasped in the hand of a user. With the grip 18 in the user's hand, the thumb, or the index finger and thumb on the user's hand, can be used to rotate an actuating element 20, which repositions a working element 22 at the distal end 16 of the instrument 10 between a first position, shown in FIGS. 1 and 4, and a second position shown in FIG. 3.

It should be understood that the precise configuration of the instrument 10, and the nature of the working element 22, may vary considerably from that shown in the drawings.

In this case, the working element 22, which is in the form of a hook, is connected to the body 12 through a pin 24. The pin 24 serves as a means for mounting the working element 22 on the body for movement relative to the body between first and second positions by pivoting movement of the working element 22 about an axis 26.

Means is provided at 28 for moving the working element 22 selectively between the first and second positions, from a location remote therefrom, and for maintaining/locking the working element 22 in each of the first and second positions. More particularly, the means 28 maintains/locks the working element 22 in every position between the first and second positions by structure described in detail below.

More particularly, the means 28 includes a slide subassembly at 30 made up of an elongate rod 32, a slide block 34, a guide pin 36 and a threaded coupler 38. The rod 32 has an end 40 that is threadably engaged within a through bore 42 in the slide block 34. The slide block 34 is movable guidingly against an inside surface 44 on a hollow sleeve 46 lengthwise of the instrument 10 between a first, retracted state, shown in FIG. 3, and a second, extended state, shown in FIG. 4.

The distal end 48 of the rod 32 is joined to the working element 22 through a link 50. The link 50 has one end 52 pivotably connected to the distal rod end 48 through a pin 54, and an opposite end 56 pivotably connected to a midportion of the working element 22 through a pin 58.

Through this arrangement, forward movement of the rod 32 causes the link 50 to drive the working element 22 in the direction of the arrow 60, in FIG. 3, from the FIG. 3 position to the FIG. 4 position. Retraction of the rod 32 effects opposite pivoting movement of the working element 22.

Fore and aft movement of the rod 32 is effected through cooperation between the actuating element 20 and the coupler 38. The coupler 38 has a hollow, cylindrical shape which closely conforms to, and surrounds, the outer surface 62 of the sleeve 46. The guide pin 36 extends radially through the coupler 38, through a guide slot 66 in the sleeve 46, through the slide block 34, through a separate guide slot 68 on the sleeve 46 and into the coupler 38 at a diametrically opposite location. The slots 66, 68 have a sufficient lengthwise extent to permit the pin 36 to be guided in a fore and aft direction to allow the rod 32 to move the working element 22 fully between the first and second positions therefor.

The coupler 38 has external threads 70 which engage internal threads 72 on the actuating element 20. The actuating element 20 is restrained against lengthwise movement between facing shoulders 74, 76 on the body 12. As a result, rotation of the actuating element 20 relative to the coupler 3 8 in one direction causes forward movement of the slide subassembly whereas opposite rotational movement effects rearward movement thereof.

With this arrangement, the working element 22 is automatically maintained/locked in every position that it assumes. That is, the working element 22 cannot be repositioned by exerting a force on the working element 22, regardless of its magnitude. The only way that the working element 22 can be moved in either direction is by rotation of the actuating element 20. Any pressure applied to the working element 22 to effect its repositioning would result in a binding force between the threads 70, 72 so as to inhibit rotation between the actuating element 20 and the coupler 38. Substantially the same amount of torque 20 will effect movement of the working element 22 throughout its entire range.

A further advantage of the instrument is that it can be rolled around its length in the user's hand while maintaining the same accessibility to the actuating element 20. This facilitates operation of the instrument with the same facility with the instrument rotated through a full 360° about its length.

The instrument 10 also lends itself to assembly and disassembly. The grip 18 serves as the foundation of the instrument 10. A nipple 78 has one end 79 threaded into a stepped bore 80 in the grip 18. The opposite nipple end 82 threads inside of the sleeve 46. A cap 84 is removably held in place by a pin 86. With the cap 84 removed, the sleeve 46 can be threaded into place after which the actuating element 20 can be threaded onto the coupler 38. With the pin 86 in place, the actuating element 20 remains captive between the grip 18 and the cap 84.

Preferably the nipple 78 and sleeve 46 are made hollow such that a communication passageway is defined continuously between the rearwardmost surface 88, through the bore 80, the nipple 78, the sleeve 46, and the open distal end 90 of the sleeve 46. This facilitates flushing of the instrument as with a sterilizing fluid.

An end fitting 92 is provided in the grip 18 to removably accept a cap 94 that can be used to block the aforementioned fluid passageway.

In FIG. 5, a modified form of instrument is shown at 10'. The instrument 10' has a body 12' and a slide subassembly 30' with a rod 32', the same as the instrument 10. The principal difference is that the working element consists of a movable jaw 96 which is pivotably connected to the body 12' through a pin 98. The jaw 96 cooperates with a fixed jaw 100 on the body 12' and is movable relative thereto between a closed position, shown in solid lines in FIG. 5, and an open position, shown in phantom lines. The previously described mechanism will releasably maintain/lock the jaws 96, 100 in the open and closed positions, and all positions therebetween.

The above mechanism can be utilized in any instrument having a translatable actuating element.

The foregoing disclosure of specific embodiments is intended to be illustrative of the broad concepts comprehended by the invention.

I claim:

1. A surgical instrument comprising:
   a body having a proximal end and a distal end spaced longitudinally from the proximal end;
   a working element,
   first means for mounting the working element on the body for movement relative to the body in first and second opposite directions between first and second positions; and
   second means on the body for a) moving the working element selectively between the first and second positions from a location remote from the working element, and b) maintaining the working element in each of the first and second positions such that the working element is substantially fixed against movement in either of the first and second opposite directions with the working element in each of the first and second positions, said second means including
   an actuating element manually pivotable relative to the body to pivot a first helical thread, said actuating element being substantially fixed against longitudinal movement relative to the body,
   a reciprocable control member disposed around said body and longitudinally movable relative thereto, said reciprocable control having a second helical thread engaging said first helical thread,
   a longitudinally extending slot in said body,
   a control element extending through said body and reciprocable longitudinally relative to the body, said control element connected to the working element for actuating movement of the working element between the first and second positions, and
   a guide pin extending into and longitudinally movable in said body slot, said guide pin being secured to said reciprocable control member and to said longitudinal control element.

2. The surgical instrument according to claim 1 wherein the second means comprises means for maintaining the working element in a third position.

3. The surgical instrument according to claim 1 wherein the second means comprises means for preventing the working element from moving from its second position towards its first position by manipulation of the working element.

4. The surgical instrument according to claim 3 wherein the working element is movable from its first position towards its second position as an incident of the actuating element moving relative to the body in a first direction and the second means comprises means for allowing the working element to move from its second position towards its first position only by moving the actuating element relative to the body oppositely to the first direction.

5. The surgical instrument according to claim 1 wherein the third means comprises means for mounting the actuating element on the body for rotational movement relative to the body about a first axis.

6. The surgical instrument according to claim 5 wherein the body has a length that is substantially parallel to the first axis.

7. The surgical instrument according to claim 6 wherein the first means comprises means for mounting the working element on the body for pivoting movement of the working element relative to the body about a second axis.

8. The surgical instrument according to claim 7 wherein the first axis is transverse to the second axis.

9. The surgical instrument according to claim 1 wherein the body is substantially cylindrical with a tubular opening therein, and the longitudinal control element includes a slide element substantially matching the tubular opening, wherein said guide pin is secured to said slide element.

10. The surgical instrument according to claim 9 wherein the actuating element is rotatable selectively in first and second opposite directions and the first and second helical threads cooperate for moving the slide element to change the working element from its first position into its second position as an incident of the actuating element rotating in one of the first and second opposite directions.

11. The surgical instrument according to claim 9 wherein the body cylindrical opening facilitates flushing of the surgical instrument.

12. The surgical instrument according to claim 11 including a cap and means for removably attaching the cap to the body so that the cap blocks the body cylindrical opening.

13. The surgical instrument according to claim 1 wherein the working element comprises a first jaw and there is a second jaw on the body and with the first jaw in the first position the first and second jaws are closed against each other and with the first jaw in the second position, the first and second jaws are in an open state.

14. A surgical instrument comprising:
   a body having a proximal end and a distal end spaced longitudinally from the proximal end and a longitudinally extending slot intermediate said ends;
   a control element extending through said body;
   a working element mounted on the body distal end for movement relative to the body in first and second opposite directions responsive to longitudinal movement of the control element relative to the body;
   a manually engageable element pivotable about the body to pivot a first helical thread, said manually engageable element being substantially fixed against longitudinal movement relative to the body;
   a reciprocable control member disposed around said body and longitudinally movable relative thereto, said reciprocable control member having a second helical thread engaging said first helical thread; and
   a guide pin extending through and longitudinally movable in said body slot and having spaced ends, said guide pin being secured on its one end outside the body to said reciprocable control member and on its other end inside the body to said longitudinal control element.

15. The surgical instrument of claim 14, wherein said first and second helical threads engage through greater than 360° degrees whereby frictional engagement between said threads substantially fix the working element against movement in either of the first and second opposite directions in response to a force applied to the working element.

16. The surgical instrument of claim 14, wherein said second helical thread projects outwardly and said first helical thread projects inwardly, and further comprising:
   a handle on said body and defining a pair of shoulders longitudinally spaced an amount substantially equal to the longitudinal dimension of the manually engageable element, said manually engageable element being disposed between said shoulders.

* * * * *